US012142381B1

(12) United States Patent
Farmer et al.

(10) Patent No.: US 12,142,381 B1
(45) Date of Patent: Nov. 12, 2024

(54) SYSTEMS AND METHODS FOR OFFERING PRODUCTS BASED ON MEDICAL ASSESSMENTS

(71) Applicant: United Services Automobile Association (USAA), San Antonio, TX (US)

(72) Inventors: William Daniel Farmer, Carrollton, TX (US); Anto Chirayil Thomas, Coppell, TX (US); Pooja Krishnaswamy, Cedar Park, TX (US); Daniel Scott Veibell, Plano, TX (US); Seth E. Ethington, McKinney, TX (US); Timothy Shiveley, Farmers Branch, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 424 days.

(21) Appl. No.: 17/003,736

(22) Filed: Aug. 26, 2020

Related U.S. Application Data

(60) Provisional application No. 62/893,640, filed on Aug. 29, 2019.

(51) Int. Cl.
*G16H 50/30* (2018.01)
*G06Q 40/08* (2012.01)
(Continued)

(52) U.S. Cl.
CPC .............. *G16H 50/30* (2018.01); *G06Q 40/08* (2013.01); *G06V 40/167* (2022.01);
(Continued)

(58) Field of Classification Search
None
See application file for complete search history.

(56) References Cited

U.S. PATENT DOCUMENTS

| | | | |
|---|---|---|---|
| 2009/0185723 A1* | 7/2009 | Kurtz | G06V 40/50 |
| | | | 382/118 |
| 2012/0147167 A1* | 6/2012 | Manson | G06V 20/64 |
| | | | 382/118 |

(Continued)

OTHER PUBLICATIONS

Lee, B. J., & Kim, J. Y. (2014). "Predicting visceral obesity based on facial characteristics." BMC Complementary and Alternative Medicine, 14, n/a-248. doi:http://dx.doi.org/10.1186/1472-6882-14-248 (Year: 2014).*

(Continued)

*Primary Examiner* — Rachel L. Porter
(74) *Attorney, Agent, or Firm* — Fletcher Yoder, P.C.

(57) ABSTRACT

A system in accordance with present embodiments includes a device comprising a sensor configured to detect sensed data for an individual. The sensed data comprises data related to health of the individual. The system also includes a health analysis system communicatively coupled to the device. The health analysis system comprises a memory and a processor. The memory is configured to store instructions that cause the processor to receive the sensed data from the device, analyze the sensed data to determine health trend data for the individual, retrieve group health trend data associated with the health trend data for the individual, generate a predicted health trend for the individual based at least in part on a comparison between the health trend data for the individual and the group health trend data, and adjust offered products, premiums, or both, based on predicted health trend for the individual.

20 Claims, 3 Drawing Sheets

(51) Int. Cl.
  *G06V 40/16*     (2022.01)
  *G16H 50/20*     (2018.01)
  *G16H 50/70*     (2018.01)
  *A61B 5/00*      (2006.01)
  *A61B 5/02*      (2006.01)
  *G16H 20/13*     (2018.01)

(52) U.S. Cl.
  CPC .......... *G06V 40/171* (2022.01); *G06V 40/174* (2022.01); *G16H 50/20* (2018.01); *G16H 50/70* (2018.01); *A61B 5/02* (2013.01); *A61B 5/681* (2013.01); *G16H 20/13* (2018.01)

(56) References Cited

U.S. PATENT DOCUMENTS

| | | | | |
|---|---|---|---|---|
| 2014/0348403 | A1* | 11/2014 | Kurtz | A61B 5/0059 |
| | | | | 382/128 |
| 2018/0150609 | A1* | 5/2018 | Kim | G06N 3/04 |
| 2018/0253906 | A1* | 9/2018 | Tran | A43B 3/34 |
| 2019/0333220 | A1* | 10/2019 | DeLuca | G06T 7/90 |
| 2019/0344120 | A1* | 11/2019 | Fung | A63B 22/0046 |
| 2022/0156844 | A1* | 5/2022 | Myers | G06Q 40/08 |

OTHER PUBLICATIONS

"As predictor of age, blood over face proves big disgrace." Apr. 7, 2015/. University Wire, Apr. 7, 2015, https://dialog.proquest.com/professional/docview/1670607148?accountid=131444 (accessed Jun. 11, 2024).—(Year: 2015).*

* cited by examiner

SYSTEMS AND METHODS FOR OFFERING PRODUCTS BASED ON MEDICAL ASSESSMENTS

CROSS-REFERENCE TO RELATED APPLICATIONS

This application claims priority from and the benefit of U.S. Provisional Application Ser. No. 62/893,640, entitled "SYSTEMS AND METHODS FOR OFFERING PRODUCTS BASED ON MEDICAL ASSESSMENTS," filed Aug. 29, 2019, which is hereby incorporated by reference in its entirety for all purposes.

BACKGROUND

The present disclosure relates generally to a health analysis system that facilitates providing insurance products to users. More specifically, the present disclosure relates to adjusting rates and availability of insurance products for users based on medical assessments of the users.

This section is intended to introduce the reader to various aspects of art that may be related to various aspects of the present disclosure, which are described and/or claimed below. This discussion is believed to help provide the reader with background information to facilitate a better understanding of the various aspects of the present disclosure. Accordingly, it is understood that these statements are to be read in this light, and not as admissions of prior art.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In an embodiment, a health analysis system includes a sensor that detects individual health data for an individual, one or more processors, and one or more memory devices. The one or more memory devices store instructions that cause the one or more processors to receive the individual health data from the sensor, and retrieve group health data for a group of individuals associated with the individual health data for the individual. The instructions also cause the one or more processors to generate a predicted health trend for the individual based at least in part on comparing the group health data and the individual health data, and adjust a health-related product or service based on the predicted health trend for the individual.

In an embodiment, one or more non-transitory, tangible, computer-readable media includes instructions that, when executed by one or more processors, cause the one or more processors to receive individual biometric data from a biometric sensor, determine individual health data based on the individual biometric data, and retrieve group health data for a group of individuals associated with the individual health data for the individual. The instructions also cause the one or more processors to generate a predicted health trend for the individual based at least in part on a comparison between the group health data and the individual health data, and adjust a health-related product or service based on the predicted health trend for the individual.

In an embodiment, a method includes receiving multiple images of a face of an individual from a camera at multiple times, determining individual health trend data based at least in part on the multiple images of the face of the individual, and retrieving group health trend data for a group of individuals associated with the individual health trend data. The method also includes generating a predicted health trend for the individual based at least in part on comparing the group health trend data and the individual health trend data and adjusting a health-related product or service based on the predicted health trend for the individual.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
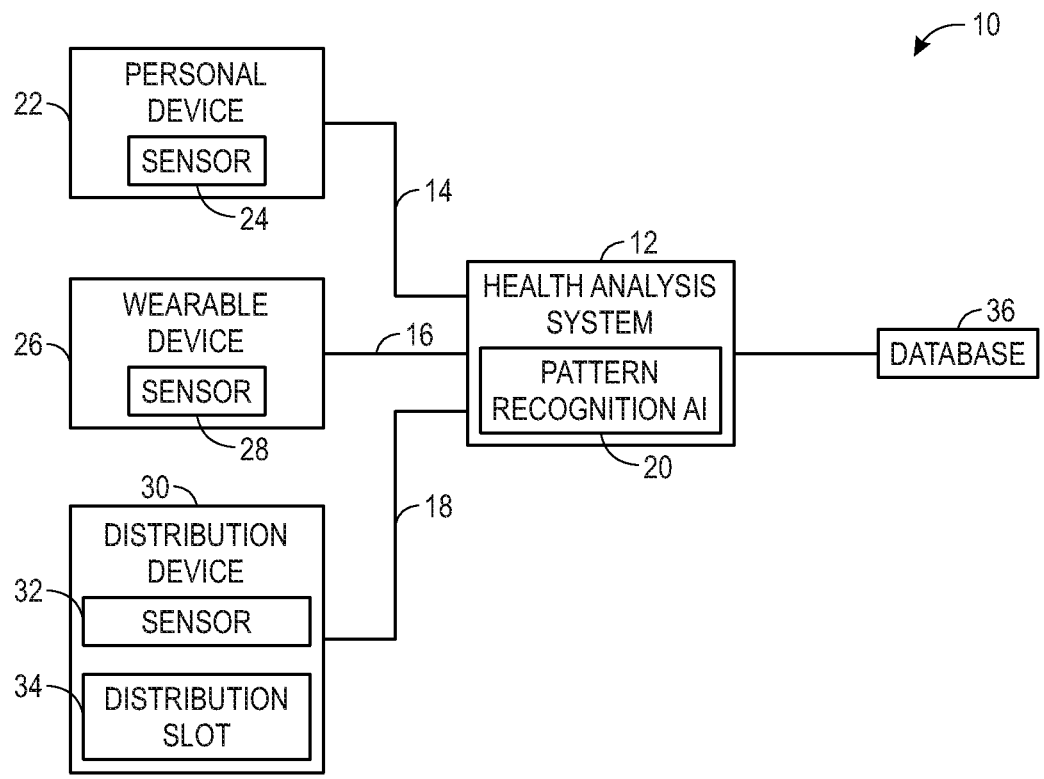
FIG. 1 is a block diagram of an insurance management system, in accordance with embodiments described herein.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Actuarial models may be used to determine survivorship of people from a certain population (e.g., for a certain age of the people, a certain region of the people, or a certain generation of the people). The determined survivorship of the people may be used to determine how to set insurance premiums for and/or offer products to users. These models may take into account factors such as disability, morbidity, mortality (e.g., life expectancy), fertility and other survivorship-related characteristics of users. For example, life expectancy may indicate a risk level for an insurance provider when considering some products (e.g., life-insurance plans). Life expectancy may be determined based on an age of the individual using mortality tables or actuarial tables. However, the actuarial models may only provide survivorship metrics associated with people from a large group (e.g., people of a certain age or living in a certain region), and may not be sufficiently granular to take into account information related to a user's specific health conditions (e.g., the user's body mass index, illnesses suffered by the user, or whether the user is taking prescribed medication). As such, it is now recognized that more accurately determining survivorship for users based on their specific health conditions may lead to better accuracy in determining appropriate insurance premiums and/or products.

With the foregoing in mind, the present disclosure provides an insurance system that adjusts premiums and/or products for users based on medical assessments (e.g., samples, tests, or measurements) of the users. The medical assessments may provide real-time sensed data (e.g., facial data, biometric data, or distribution data) to a health analysis system of the insurance system to determine health trend data (e.g., data indicative of a health condition of the user over a period of time) for a user. The health analysis system retrieves group health trend data (e.g., health trend data of other users with similar health trend data) associated with the health trend data for the user. The health analysis system generates a predicted health trend for the user based at least in part on a comparison between the health trend data and the group health trend data. The insurance system may adjust the premiums and/or products based at least in part on the predicted health trend data for the user. As the predicted health trend data and/or the health trend data of particular users may more accurately assess the survivorship factors (e.g., disability, morbidity, mortality, fertility and other survivorship-related characteristics) of users than actuarial models, adjustments to the premiums and/or products may be better suited for the users. The products may include life insurance products (e.g., term life insurance, whole life insurance, or universal life insurance), health insurance products (e.g. preferred provider organization "PPO", health maintenance organization "HMO", or health savings account "HSA"), or any suitable insurance product. The premiums include the respective costs of the products. In view of the foregoing, a benefit of present embodiments to users includes rewarding healthy behavior.

Present embodiments may provide automated alerts based on a technologically-rooted solution to health issues and networking issues (e.g., confidentiality concerns). Indeed, present embodiments improve operational efficiency by providing direct communication with individuals and facilitating direct comparison of obtained (and often confidential) data with established group data. The individual data may be concealed and encrypted to maintain confidentiality, while results from comparison of individual and group data may be provided to the user and other stakeholders. In some embodiments, relevant group data may be stored on a user device. For example, once a user is identified as having a correlation to a particular set of group data (e.g., the user has a characteristic in common with a specified group), that group data may be stored on the individual's personal device (e.g., smart phone). This may be beneficial because comparison and analysis may be performed locally on the individual's personal device. Not only does this improve efficiency of operation, it also provides the individual with control over their personal data. It should also be noted that having the various sensing mechanisms integrated with the same personal device that is hosting the application data improves functionality for computing by increasing communication efficiency.

FIG. 1 illustrates a block diagram of an insurance system 10 that may adjust insurance premiums and/or products based on health trend data, in accordance with embodiments described herein. The insurance system 10 may include a health analysis system 12 that determines the health trend data (e.g., data indicative of a health condition of the user over a period of time) based at least in part on sensed data (e.g., data, associated with the user and collected by a sensor, that may facilitate determining the user's health trend data). The sensed data may include facial data 14 (e.g., data points used to identify features of the user's face), biometric data 16 (e.g., pulse data, oxygen level data, blood sample data, eye dilation data, eye characteristic data, or odor or scent data), medicine distribution data 18, weight data, height data, pigment data, and so on.

In some embodiments, the health analysis system 12 includes a pattern recognition system 20 (e.g., artificial intelligence system) that identifies current and/or potential health problems (e.g., heart condition, respiratory disease, or diabetes) based on the health trend data (e.g., data indicating current and/or historic blood pressure levels, oxygen levels, or glucose levels). For example, a personal device 22 (e.g., a smartphone, tablet, laptop computer, or wearable device) having a first sensor 24 (e.g., camera) may provide pictures of a user (e.g., sensed data) to the health analysis system 12. The health analysis system 12 may extract the facial data 14 from the pictures and compare the facial data 14 of the user over a period of time. Based on detected changes in the facial data 14 (e.g., health trend data), the pattern recognition system 20 of the health analysis system 12 may identify current and/or potential health problems associated with the user. The personal device 22 may be any suitable device for providing the facial data 14 to the health analysis system 12.

In some embodiments, the insurance system 10 includes a wearable device 26 that provides, for example, the biometric data 16 to the health analysis system 12 for identifying current and/or potential health problems associated with the user. In this example, the wearable device 26 may include a second sensor 28 that takes a medical sample (e.g., sweat, blood draw, or odor) or measurement (e.g., blood pressure level, sleep patterns, or glucose levels) of the user. For example, the wearable device 26 may take a sweat sample of the user and perform tests of the sweat sample. Based on the test results of the sweat sample, the wearable device 26 may generate the biometric data 16 and output the biometric data 16 to the health analysis system 12. The health analysis system 12 may receive the biometric data 16 and analyze the biometric data 16 as it is acquired and input over time. As an example of such analysis, present embodiments may compare biometric data 16 from tests of multiple samples taken over a period of time. Based on the changes in the biometric data 16 (e.g., health trend data), the pattern recognition system 20 of the health analysis system 12 may identify current and/or potential health problems associated with the user. As such, in some embodiments, the wearable device 26 may be a dedicated medical test device. In alternative or additional embodiments, the wearable device 26 may be a smart watch or other suitable device that collects at least one medical sample or measurement.

In some embodiments, the insurance system 10 includes a distribution device 30 that provides the medicine distribution data 18 (e.g., data indicating whether the user has taken a medicine or compound) to the health analysis system 12 for identifying current and/or potential health risks associated with the user. The distribution device 30 may dispense the medicine or compound for the user to a distribution slot 34 of the distribution device 30. The distribution device 30 may include a third sensor 32 that detects whether the medicine or compound was removed from the distribution slot 34. Further, the third sensor 32 may determine that the user has taken the medication or compound in response to the medication or compound being removed from the distribution slot 34, and output the medicine distribution data 18 to the health analysis system 12. The health analysis system 12 may receive the medicine distribution data 18 and analyze the medicine distribution data 18 over time. Based on trends in the medicine distribution data 18, the health analysis system 12 may identify potential health risks for the user.

For example, the distribution device 30 may distribute a heart medication to a user for a diagnosed heart condition at prescribed times. The third sensor 32 may detect, for example, whether the medicine was removed from a distribution slot 34 of the distribution device 30 within a predetermined amount of time from distribution, and output the medicine distribution data 18. The medicine distribution data 18 may indicate that the user is not taking their heart medicine. Thus, the health analysis system may determine that the user has an increased risk of having a heart attack.

Moreover, the insurance system 10 may include a database 36 that stores health trend data. As set forth above, the health analysis system 12 may receive sensed data (e.g., facial data 14, biometric data 16, or medicine distribution data 18) from various devices (e.g., the personal device 22, the wearable device 26, or the distribution device 30) and generate health trend data based on the sensed data. In additional or alternative embodiments, the health trend data may be stored, for example, in a memory device of the health analysis system 12. Based on the aggregate health trend data stored in the database or memory device, the health analysis system 12 may determine group health trend data for a group of individuals with similar circumstances (e.g., age or current health conditions).

In addition to the database 36 described above, it should be noted that the health analysis system 12 may have access to other databases that may provide additional information related to medical assessments of the users. For instance, the other databases may include the user's health history information indicating past health issues, allergies, surgeries, etc. In some embodiments, the other databases may include the user's family health history. As some conditions may be genetically passed down, the user's family health history may provide information regarding potential conditions that may not be detected via the user's health trend data. For example, a user may have a condition that has a high likelihood of being passed down from a parent to their child. However, the condition may not manifest itself immediately. The condition may be rare, even among other individuals with similar health trend data. As such, the group health trend data may not include the user's potential condition. However, storing the user's family health history in the other database may provide data regarding the conditions that may be genetically passed down to the user to the health analysis system 12 to determine more accurate results. This kind of data may be included or specifically excluded from relevant analysis procedures discussed herein.

Figure 2:
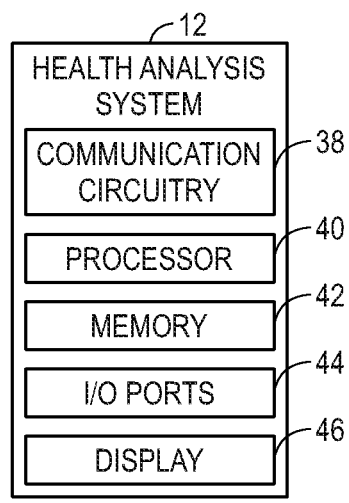
FIG. 2 is a block diagram of a health analysis system of FIG. 1, in accordance with embodiments described herein.

To perform some of the actions set forth above, health analysis system 12 may include certain components to facilitate these actions. FIG. 2 is a block diagram of example components within the health analysis system 12. For example, the health analysis system 12 may include communication circuitry 38, a processor 40, a memory 42, input/output (I/O) ports 44, a display 46, and the like. The communication circuitry 38 provides for wireless or wired communication. In some embodiments, the communications circuitry 38 may include antennas, radio transceiver circuits, and signal processing hardware and/or software (e.g., hardware or software filters, A/D converters, multiplexers amplifiers). These components may facilitate communicating over wireless communication paths via Infrared (IR) wireless communication, satellite communication, broadcast radio communication, Microwave radio communication, Bluetooth communication, Zigbee communication, Wifi communication, Ultra-high frequency communication (UHF), Near field communication (NFC), and the like.

The processor 40 may be any type of computer processor or microprocessor capable of executing computer-executable instructions. The processor 40 may also include multiple processors that may perform the operations described below.

The memory 42 may include one or more tangible, non-transitory, machine-readable media. It should be noted that non-transitory merely indicates that the media is tangible and not merely a signal. By way of example, such machine-readable media can include RAM, ROM, EPROM, EEPROM, optical disk storage, magnetic disk storage or other magnetic storage devices, or any other medium which can be used to carry or store desired program code in the form of machine-executable instructions or data structures and which can be executed by the processor 40 or by other processor-based devices. In some embodiments, the memory 42 stores instructions executable by the processor 40 to perform the presently disclosed techniques. For example, the processor 40 may execute the instructions to generate health trend data based on the received sensed data, retrieve group health trend data (e.g., health trend data of other users with similar health trend data) from the database, generate a predicted health trend for the user, provide a report or recommendation regarding adjustment of products and/or premiums for users, and/or adjust the offered products and/or premiums.

The I/O ports 44 may be interfaces that couple to other peripheral components such as input devices (e.g., keyboard, mouse, microphone), sensors, input/output (I/O) modules, and the like. The display 46 may depict data, report, recommendations, or adjustments associated with software or executable code being processed by the processor 40. In one embodiment, the display 46 may be a touch display capable of receiving inputs from a user of the health analysis system 12. The display 46 may be any suitable type of display, such as a liquid crystal display (LCD), plasma display, or an organic light emitting diode (OLED) display. Additionally, in one embodiment, the display 46 may be provided in conjunction with a touch-sensitive mechanism (e.g., a touch screen) that functions as part of a control interface for the health analysis system 12. In some embodiments, the display 46 may be transparent in that a user of the display 46 may view through the display 46 to see objects present in front of the user. In addition or in the alternative, the display 46 may be capable of projecting visualizations over real objects viewable through the display 46 (e.g., augmented reality display).

It should be noted that the components described above with regard to the health analysis system 12 are exemplary components, and the health analysis system 12 may include additional or fewer components as shown. Additionally, it should be noted that the personal device, wearable device, and/or distribution device may also include similar components as described as part of the health analysis system.

Figure 3:
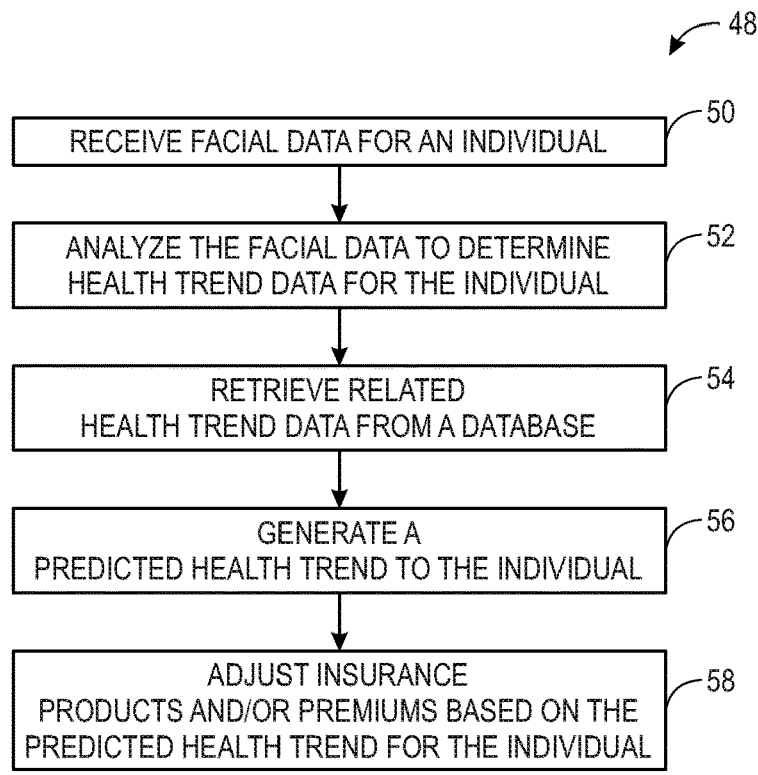
FIG. 3 is a flow chart of a method for adjusting offered products based on health trend data determined from facial data of a user, in accordance with embodiments described herein.

FIG. 3 illustrates a flow chart of a method 48 employed by the health analysis system for adjusting offered products based on health trend data determined from facial data of the user. Although the following description of the method is described in a particular order, it should be noted that the method 48 is not limited to the depicted order; and, instead, the method may be performed in any suitable order, including omitting certain blocks.

As illustrated, at block 50, the health analysis system may receive facial data (e.g., data points used to identify features of the user's face) for the user. As discussed above, the personal device (e.g., a smartphone, tablet, laptop computer, or wearable device) may include a sensor (e.g., camera) that captures an image of the user. The personal device may include an application that prompts the user to capture the image of the user (e.g., to take a selfie). The application may prompt the user to capture the image of the user at regular intervals (e.g., weekly or monthly). The personal device may determine facial data from the captured image. In such embodiments, the personal device may output the determined facial data to the health analysis system, such that the health analysis system receives the facial data from the personal device. In additional or alternative embodiments, the personal device outputs the captured image to the health analysis system. In such embodiments, the health analysis system may receive the facial data via extracting or determining the facial data from the captured image. The health analysis system may use a facial recognition algorithm to extract or determine the facial data from the captured image.

In some embodiments, the facial data may be received from other sources. For example, images of the user may be stored on a website or online database associated with the health analysis system. In such an example, the user may be prompted by the insurance provider to update a medical assessment profile photograph on the user's respective profile. In some embodiments, the health analysis system may retrieve the profile photograph of the user on a fixed interval. An input (e.g., mouse input, keyboard input, or touchscreen input) from the user interface may cause the health analysis system to retrieve the profile photograph. In another embodiment, uploading the profile photo triggers the health analysis system to retrieve the profile photograph. Further, the health analysis system may determine the facial data from the profile photograph.

Moreover, the health analysis system may include a timestamp with the facial data. The timestamp may be based on the date the profile photograph was uploaded. However, the profile photograph may be taken weeks, months, or year before being uploaded. Thus, in some embodiments, the health analysis system may include a timestamp based on a date of capture of the profile photograph. The health analysis system may be configure to analyze the metadata of the profile photograph to determine the date of capture. In some embodiments, the user may be prompted to include the date of capture when uploading the profile photograph. After determining an accurate date of capture, the method may include the step of storing the timestamp and the facial data in an application without opening the application. That is, the timestamp and the facial data may be automatically stored in the application without loading or running the application.

At block 52, the health analysis system may analyze the facial data to determine health trend data for the individual. The health analysis system may use a facial recognition algorithm to analyze the facial data. For example, the facial data may include three-dimensional facial data points used to identify features of the surface of the user's face. The facial recognition algorithm may use the facial data points to identify contours of eye sockets, nose, chin, cheeks, etc. The facial data may additionally include data points associated with wrinkles, creases, skin tags, or other features of the user's face. The facial data may be used by the facial recognition algorithm to determine a size and shape of each of the features of the user's face. The health analysis system may analyze the facial data to determine the health trend of the individual by comparing sets of facial data. Each set of facial data may be associated with a same profile or photograph of the individual from which the facial data was extracted. Further, each set of facial data may correspond to the respective timestamp. The health analysis system may compare the sets of facial data to determine changes of each of the features of the individual users with respect to time.

For example, the health analysis system may determine that a chin of the user had a first shape at a first time. The health analysis system may determine, from a second facial data set from a second image taken two years later, that the chin of the user has the second shape that is substantially the same shape as the first shape. However, during an analysis of a third data set corresponding to an image taken two months after the second image, the health analysis system may determine that the chin of the individual has a third shape that is substantially different than the second shape and the first shape. The health analysis system may determine a portion of the health trend data based at least in part on the shape of the user's chin. The health trend data may indicate that the user's chin changed significantly over a short period of time (e.g., two months) after having remained the substantially the same shape for a period of at least two years. In a similar manner, the health analysis system may determine health trend data for each feature of the user's face. Additionally, the health analysis system may track changes in any other suitable body part of the user and determine health trend data based on the changes in the user's body part, such as eyes, height, hand, nose, hair, ears, and so on. In some embodiments, the health analysis system uses a machine learning algorithm to determine the changes of each of the features of the individual users with respect to time.

At block 54, the health analysis system retrieves group health trend data from the database. The database may include health trend data of other individuals that have previously experienced health trends related or similar to the current health trend of the user. Using the example provided above, the database may include health trend data for users that had experienced a sudden change of shape of their respective chins over a short period of time. The health analysis system may analyze the health trend data of the other users in the database to determine a related group of users that had previously experienced health trends similar to the current health trends of the user (e.g., experienced a sudden change of shape of their respective chins over a short period of time). The group trend data may include the health trend data of the related group of users. In determining the related group of users, the health analysis system may consider a single type of health trend data (e.g., changes in data points associated with user's noses), multiple types of health trend data (e.g., changes in data points associated with user's noses and mouths), or overall health trend data (e.g., changes in a majority of data points of the facial data).

In some instances, the current health trend data of the user may be similar to health trend data for a large number of users. As such, the health analysis system may filter results by only retrieving health trend data for users with ages, weight, gender, and/or any other suitable physical user characteristic, similar to that of the user. The health analysis system may further filter health trend data by only retrieving health trend data for users with professions, family medical history, personal medical history, and/or any other suitable characteristic, similar to that of the user.

At block 56, the health analysis system generates a predicted health trend for the user. Each of the users associated with the health trend data retrieved from the database had previously experienced health trends similar to the current health trend of the user. For example, each of the individuals may have experienced a sudden change of shape of their respective chins over a short period of time. As the health trend data for the other users has already occurred, the health analysis system may analyze events that occurred after the health trends (e.g., after the sudden change of the shape of their respective chins), and determine or generate a predicted health trend for the user. For example, the health analysis system may determine that after the other users had experienced a sudden change of shape of their respective chins over a short period of time, seventy-eight percent of the users in the group of users experienced a heart attack within two-years of the sudden change of shape of their respective chins. Thus, based on an analysis of the health trend data of the other users and a comparison of the health trend data of the other users to the health trend data of the user, the health analysis system may generate the predicted health trend for the individual that would indicate that the user has a high risk of a heart attack within two years. The health analysis system generates the predicted health trend for the user based on an analysis of the health trend data retrieved from the database.

At block 58, the health analysis system adjusts insurance products and/or premiums based on the predicted health trend for the individual. For example, the insurance provider may generally offer life insurance policies to users. However, the insurance provider may limit life insurance policies offered to individuals based on their respective health. The health analysis system may generate a predicted health trend indicating that the user (e.g., future user) has a high risk of death within the next couple of years. Based on the predicted health trend for the individual, the health analysis system may adjust the products offered to the user such that they are not eligible for at least some types of life insurance. In another example, the predicted health trend may indicate that the user has a very low risk of death, but that the individual will likely develop a medical condition that would require the user to have frequent visits to a hospital. Based on the predicted health trend, the health analysis system may adjust the premiums to a higher rate to account for the predicted risk of hospital fees. In a further example, the user (e.g., current user) may already be a user that is currently paying a high premium. However, the predicted health trend for the individual may indicate that the user has a low risk of death or medical complications. Thus, the health analysis system may adjust the individual's premium to a lower rate.

In some embodiments, the products and premiums are adjusted for future users. That is, the predicted health trend for the user does not singularly affect the products or premiums offered to the user. Instead, the predicted health trend may adjust the products or premiums offered to future users or to users generally. The insurance provider may have set premiums for each insurance plan. As the health analysis system generates predicted health trends for users, the health analysis system may adjust the premiums and products based on overall user trends. For example, based on a plurality of predicted health trends, the health analysis system may determine that, overall, users are living longer. As such, products and premiums may be adjusted generally to account for an increased life expectancy. The health analysis may determine overall trends, and adjust the products and premiums based on the overall trends.

Figure 4:
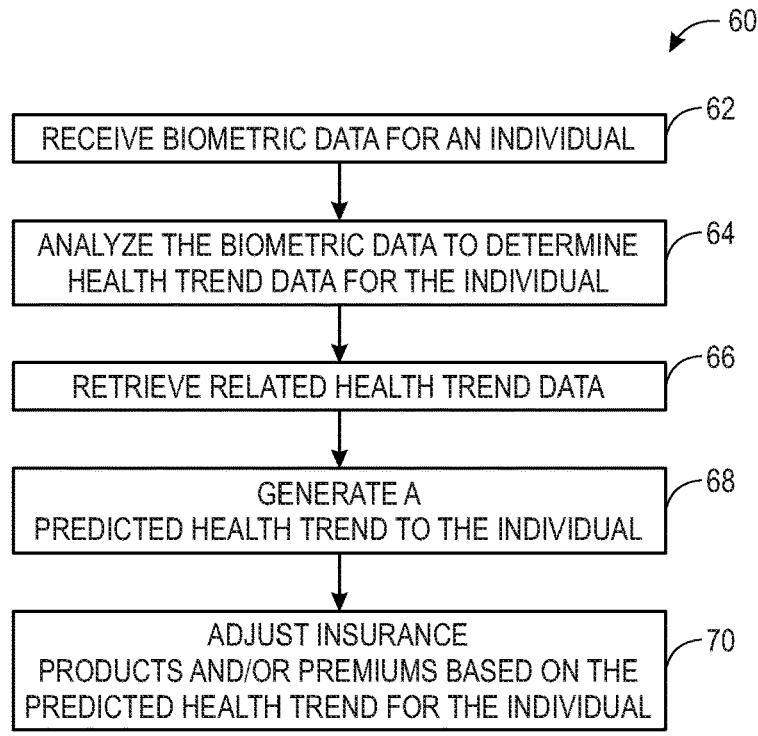
FIG. 4 is a flow chart of a method for adjusting offered products based on health trend data determined from biometric data of a user, in accordance with embodiments described herein.

FIG. 4 illustrates a flow diagram of a method 60 for adjusting offered products based on health trend data (e.g., data indicative of a health condition of the user over a period of time) determined from biometric data (e.g., data indicative of heart rate, blood pressure, sleep patterns, or glucose levels) of the user. At block 62, the health analysis system may receive the biometric data for the individual. The wearable device may be a medical test device that outputs the biometric data. As discussed above, the wearable device takes a medical sample or measurement of the user. For example, the wearable device may sample sweat from the user. In some embodiments, the wearable device monitors a heart rate, measures blood pressure, monitors sleep patterns, measures glucose levels, and so on. As such, the wearable device may include a smart watch, fitness band, or any suitable wearable device. The wearable device outputs data associated with these samples or measurement as the biometric data. The health analysis system receives the biometric data output from the wearable device.

Moreover, the health analysis system may include a timestamp (e.g., data indicating a date and/or time) corresponding to the biometric data. The timestamp may be based on the date the medical sample or measurement was performed. The method may include the step of storing the timestamp and the biometric data in an application without opening the application. That is, the timestamp and the facial data may be automatically stored in the application without loading or running the application.

At block 64, the health analysis system may analyze the biometric data to determine health trend data for the individual. In one example, the biometric data indicates a blood pressure level of the user. The biometric data may include blood pressure tests performed on the user. Each blood pressure test may be stored with a corresponding timestamp. The health analysis system may compare the blood pressure tests to determine changes in the user's blood pressure levels with respect to time. For example, a first, second, and third blood pressure test may indicate that the user has high blood pressure levels. However, a fourth and fifth blood pressure test may indicate that the user's blood pressure levels are normal. The health analysis system may determine a portion of the health trend data based at least in part on the user's blood pressure levels. The health trend data may indicate that the user's blood pressure levels were elevated, but that the user's blood pressure levels had subsequently moved to normal levels.

At block 66, the health analysis system may retrieve group health trend data (e.g., health trend data of other users with similar health trend data) from the database. As set forth above, the database may include the health trend data of other users that have previously experienced health trends similar to the current health trend of the user. For example, the database may include health trend data for users that had experienced elevated blood pressure levels that subsequently returned to normal levels for at least two blood pressure tests. The health analysis system may analyze the health trend data of the other users in the database to determine a group of users that had previously experienced similar health trends to the current health trends of the user. In some embodiments, the health analysis system may determine the group of users based on overall health trend data. That is, health trend data may include more than one metric (e.g., a heart rate, sleep patterns, or glucose levels) of the biometric data.

At block 68, the health analysis system may generate a predicted health trend for the user. As set forth above, each of the users associated with the group health trend data retrieved from the database had previously experienced similar health trends to the current health trend of the user. For example, each of the user may have experienced elevated blood pressure levels that subsequently returned to normal levels for at least two blood pressure tests. As the health trend data for the other users has already occurred, the health analysis system may analyze events that occurred after the identified similar health trends (e.g., events after the elevated blood pressure levels of the other users had returned to normal levels for at least two blood pressure tests). For example, the health analysis system may determine that after the other users had experienced blood pressure levels returning to normal levels for at least two blood pressure tests, the majority of the other user maintained normal blood pressure levels, and only seven percent of the group of users experienced a heart attack within the following two-years. The health analysis system may generate the predicted health trend for the user based on an analysis of the health trend data retrieved from the database. Thus, based on an analysis of the health trend data of the other users, the health analysis system may generate a predicted health trend for the individual that would indicate that the user has a low risk of a heart attack within two years.

At block 70, the health analysis system may adjust insurance products and/or premiums based on the predicted health trend for the individual. As set forth above, the health analysis system may adjust the insurance products and/or premiums for the user based on the predicted health trend for the user. However, in other embodiments, the health analysis system may adjust the products or premiums offered to future users or to users generally based on the predicted health trend of the user and/or overall trends determined from multiple predicted health trends determined by the health analysis system.

Figure 5:
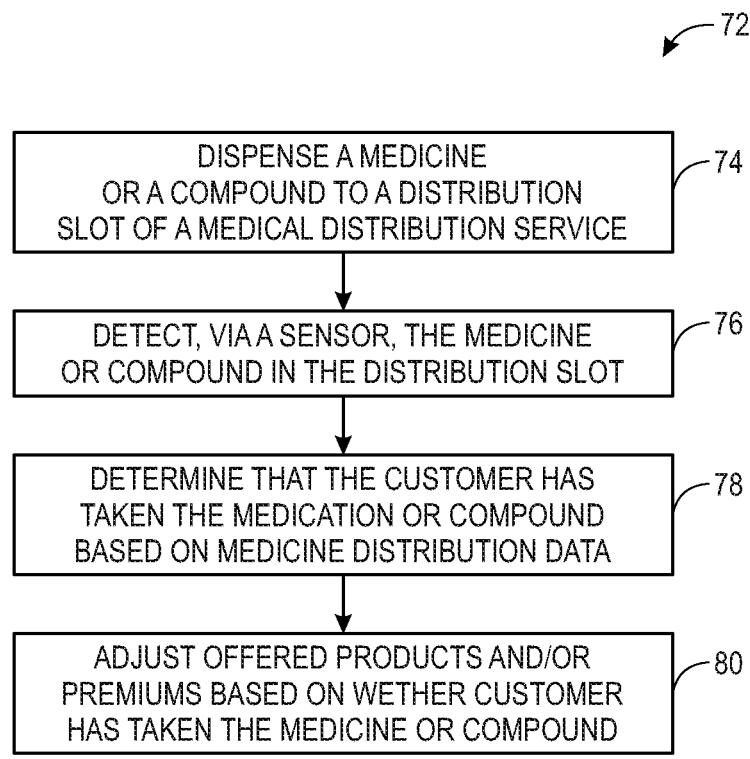
FIG. 5 is a flow chart of a method for adjusting offered products based on effectiveness of distribution of a medicine or compound to a user, in accordance with embodiments described herein.

FIG. 5. illustrates a flow chart of a method 72 for adjusting offered products and/or premiums based on effectiveness of distribution of a medicine or compound to a user. At block 74, a distribution device (e.g. medical distribution device) may dispense the medicine or compound to the distribution slot of the medical distribution device. The distribution slot may be any suitable container for holding the dispensed medicine or compound. For example, the distribution slot may hold an insulin shot. The medical distribution device may dispense the medicine (e.g., insulin shot) by moving the insulin shot from a storage compartment (e.g., portion of the medical distribution device configured to store the medicine or compound) of the medical distribution device to the distribution slot. In another example, the distribution slot may also be the storage compartment. That is, the medical distribution device may dispense the medicine or compound by unlocking the storage compartment such that the storage compartment becomes the distribution slot, and the user may access the storage compartment or distribution slot to retrieve the medicine or compound.

At block 76, the medical distribution device may detect, via a sensor, the medicine or compound in the distribution slot. After dispensing the medicine or compound the sensor may detect the medicine or compound using any suitable sensor couple to the medical distribution device. The sensor may output medicine distribution data based on the detected state of the medicine or compound. The medicine distribution data may include data points over a period of time (e.g. a first data point at zero seconds, a second data point at two seconds, etc.), where each data point indicates a binary yes or no as to whether the sensor detects the medicine or compound in the distribution slot. In some embodiments, the sensor detects an amount of the medicine or compound remaining in the distribution slot. For example, the distribution device may dispense two medical pills. The user may take one of the two medical pills. The sensor may detect that one of the two medical pills is still remaining in the distribution slot. The medical or medication distribution data may include the amount of the medicine or compound remaining in the distribution slot.

At block 78, the medical distribution device may determine that the user has taken the medication or compound based on medicine distribution data. For example, the medical distribution data may indicate that the medicine or compound was removed from the distribution slot six seconds after the medicine was dispensed into the distribution slot. As the medicine or compound was removed shortly after being dispensed, the medical distribution device may determine that the user has taken the medication or compound as prescribed. In another example, the medicine distribution data may indicate that the medicine was not removed from the distribution slot. Thus, the medical distribution device may determine that the user has not taken the medicine or compound. In another example, the medical distribution data may indicate that the medicine or compound was removed from the distribution slot three hours after the medicine was dispensed into the distribution slot. A prescription for the medicine may indicate that the medicine is to be taken every four hours. Based on the time delay between the medicine being dispensed and removed from the distribution slot, as well as the prescription of the medicine, the medical distribution device may determine that the user has not taken the medicine or that the user was not timely in taking the medicine.

In some embodiments, the medical distribution device determines that the user has taken the medicine or compound when the medicine or compound is removed from the distribution slot within a predetermined amount of time. For example, the predetermined amount of time for removing the medicine or compound from the distribution slot may be five minutes. Therefore, when the medicine or compound is removed from the distribution slot within five minutes, the medical distribution device will determine that the user has taken the medicine or compound. However, when the medicine or compound is removed from the distribution device after five minutes, the medical distribution device will determine that the user has not taken the medicine or compound.

In some embodiments, the medical distribution device includes a remote sensor. The remote sensor may be separate from the medical distribution device and may monitor the user to determine whether the user has taken (e.g., ingested or applied) the medicine or compound. For example, the distribution device may dispense a medicine for lowering blood pressure into the distribution slot. The medicine for lowering blood pressure may lower the user's blood pressure to an expected level within fifteen minutes of taking the medicine. The remote sensor may be disposed in a wearable device associated with the user. The remote sensor may monitor the blood pressure level of the user. The medical distribution device may determines that the user has taken the medicine or compound when the remote sensor detects the blood pressure level of the user lowering to the expected level following distribution of the medicine or compound.

In some embodiments, the health analysis system receives the medicine distribution data from the sensor and determine that the user has taken the medication or compound based on medicine distribution data.

At block 80, the health analysis system may adjust offered products and/or premiums based on whether user has taken the medicine or compound. In some embodiments, the health analysis system receives the medicine distribution data (e.g., or the determination that the user has taken the medicine or compound and perform an analysis based on a period of time. For example, the health analysis system may perform an analysis over the past six months. Based on trends in the medicine distribution data and/or distribution trends based on determinations that the user has taken the medicine or compound, the health analysis system may identify potential health risks for the user. For example, the health analysis system may determine that the user has only taken forty percent of their dispensed heart medication over the past six months. Taking only forty percent of the heart medication may significantly increase the risk of heart failure or other complications. As such, failing to take medication may affect life expectancy and other related factors considered in insurance products or premiums. Thus, the health analysis system may adjust offered products and/or premiums for the user based on whether the user has taken the medicine or compound.

In some embodiments, current individual users may have a contract with the insurance provider indicating that the user's premium is based on an agreement that the user will take at least a predetermined percentage of their prescribed medicine or compound. For example, the user may agree to take at least ninety-three percent of their medicine or compound to retain their current premium. In an example, the health analysis system may determine that the individual has only taken eighty-two percent of their medicine or compound over the past six months. Based on the user's failure to take the predetermined percentage of their prescribed medicine or compound health analysis system may adjust offered products and/or premiums for the user.

In other embodiments, the health analysis system adjusts the products or premiums offered to future users or to users generally based on whether an overall trend indicates that users take their prescribed medicine or compound. For example, the overall trend may indicate that on average, users only take eighty-five percent of their prescribed medicine or compound. Only taking eighty-five percent of their prescribed medicine or compound may indicate a generally heightened risk of complications. Thus, based on the generally heightened risk, the health analysis may appropriately adjust the insurance products and/or premiums offered to future users or to users generally. That is, the insurance provider may increase the premium or withdraw certain products to compensate or mitigate the likely costs associated with the generally heightened risk.

While only certain features of disclosed embodiments have been illustrated and described herein, many modifications and changes will occur to those skilled in the art. It is, therefore, to be understood that the appended claims are intended to cover all such modifications and changes as fall within the true spirit of the present disclosure.

The invention claimed is:

1. A health analysis system comprising:
 a sensor configured to detect individual health data for an individual, wherein the sensor comprises a camera;
 one or more processors; and
 one or more memory devices, wherein the one or more memory devices are configured to store instructions that cause the one or more processors to:
 receive a first image of a face of an individual at a first time from the camera;
 receive a second image of the face of the individual at a second time from the camera;
 determine three-dimensional facial data points in the first image and the second image;
 determine individual health trend data in the second image based on applying a facial recognition algorithm to the three-dimensional facial data points to determine a change in a size, a shape, or both, of one or more facial features of the individual from the first image to the second image;
 retrieve group health trend data for a group of individuals associated with the individual health trend data, wherein the group health trend data comprises a change in a size, a shape, or both, of one or more facial features of each individual of the group of individuals;
 identify one or more events over a time period associated with the group health trend data, wherein the time period comprises a time after the change in the size, the shape, or both, of the one or more facial features of the group of individuals;
 generate a predicted health trend for the individual based at least in part on the one or more events over the time period and comparing the group health trend data and the individual health trend data; and
 adjust an insurance premium based on the predicted health trend for the individual.

2. The health analysis system of claim 1, wherein the one or more memory devices are configured to store instructions that cause the one or more processors to:
 receive a first timestamp corresponding to the first time, wherein the first timestamp is associated with the first image; and
 receive a second timestamp corresponding to the second time, wherein the second timestamp is associated with the second image.

3. The health analysis system of claim 2, wherein the one or more memory devices are configured to store instructions that cause the one or more processors to determine the individual health trend data based at least in part on the first timestamp, the second timestamp, or both.

4. The health analysis system of claim 1, wherein the individual health trend data comprises a change in the three-dimensional facial data points associated with a chin of the individual, a nose of the individual, a mouth of the individual, or any combination thereof from the first image to the second image.

5. The health analysis system of claim 1, wherein the group of individuals shares one or more physical characteristics with the individual.

6. The health analysis system of claim 5, wherein the one or more physical characteristics comprise an age, a weight, a gender, or any combination thereof.

7. The health analysis system of claim 1, wherein the group of individuals shares a family medical history, a personal medical history, or both, with the individual.

8. A method comprising:
 receiving a first image of a face of an individual at a first time from the camera;
 receiving a second image of the face of the individual at a second time from the camera;
 determining three-dimensional facial data points in the first image and the second image;
 determining individual health trend data in the second image based on applying a facial recognition algorithm to the three-dimensional facial data points to determine a change in a size, a shape, or both, of one or more facial features of the individual from the first image to the second image;

retrieving group health trend data for a group of individuals associated with the individual health trend data, wherein the group health trend data comprises a change in a size, a shape, or both, of one or more facial features of each individual of the group of individuals;

identifying one or more events over a time period associated with the group health trend data, wherein the time period comprises a time after the change in the size, the shape, or both, of the one or more facial features of the group of individuals;

generating a predicted health trend for the individual based at least in part on the one or more events over the time period and comparing the group health trend data and the individual health trend data; and adjusting an insurance premium based on the predicted health trend for the individual.

9. The method of claim 8, comprising:

receiving a first timestamp corresponding to the first time, wherein the first timestamp is associated with the first image; and receiving a second timestamp corresponding to the second time, wherein the second timestamp is associated with the second image.

10. The method of claim 9, wherein determining the individual health trend data is based at least in part on the first timestamp, the second timestamp, or both.

11. The method of claim 8, wherein the group of individuals shares one or more physical characteristics with the individual.

12. The method of claim 11, wherein the one or more physical characteristics comprise an age, a weight, a gender, or any combination thereof.

13. The method of claim 8, wherein the group of individuals shares a family medical history, a personal medical history, or both, with the individual.

14. The method of claim 8, wherein adjusting the insurance premium comprises limiting insurance product eligibility, increasing a rate, decreasing the rate, or any combination thereof.

15. One or more non-transitory, tangible, computer-readable media comprising instructions that, when executed by one or more processors, cause the one or more processors to:

receive a first image of a face of an individual at a first time from a camera;

receive a second image of the face of the individual at a second time from the camera;

determine three-dimensional facial data points in the first image and the second image;

determine individual health trend data in the second image based on applying a facial recognition algorithm to the three-dimensional facial data points to determine a change in a size, a shape, or both, of one or more facial features of the individual from the first image to the second image;

retrieve group health trend data for a group of individuals associated with the individual health trend data, wherein the group health trend data comprises a change in a size, a shape, or both, of one or more facial features of each individual of the group of individuals;

identify one or more events over a time period associated with the group health trend data, wherein the time period comprises a time after the change in the size, the shape, or both, of the one or more facial features;

generate a predicted health trend for the individual based at least in part on the one or more events over the time period and comparing the group health trend data and the individual health trend data; and adjust an insurance premium based on the predicted health trend for the individual.

16. The one or more non-transitory, tangible, computer-readable media of claim 15, wherein the instructions, when executed by the one or more processors, cause the one or more processors to:

receive a first timestamp corresponding to the first time, wherein the first timestamp is associated with the first image; and receive a second timestamp corresponding to the second time, wherein the second timestamp is associated with the second image.

17. The one or more non-transitory, tangible, computer-readable media of claim 16, wherein the first timestamp is based on a first date of capture of the first image and the second timestamp is based on a second date of capture of the second image.

18. The one or more non-transitory, tangible, computer-readable media of claim 16, wherein the instructions, when executed by the one or more processors, cause the one or more processors to store the first timestamp, the second timestamp, or both in an application.

19. The one or more non-transitory, tangible, computer-readable media of claim 16, wherein the instructions, when executed by the one or more processors, cause the one or more processors to determine the individual health trend data based at least in part on the first timestamp, the second timestamp, or both.

20. The one or more non-transitory, tangible, computer-readable media of claim 15, wherein the individual health trend data comprises a change in the three-dimensional facial data points associated with a chin of the individual, a nose of the individual, a mouth of the individual, or any combination thereof from the first image to the second image.

* * * * *